United States Patent
Isobe et al.

(10) Patent No.: US 8,556,734 B2
(45) Date of Patent: Oct. 15, 2013

(54) FLEXIBLE WIRE

(75) Inventors: Hiroshi Isobe, Iwata (JP); Takayoshi Ozaki, Iwata (JP)

(73) Assignee: NTN Corporation, Osaka (JP)

( * ) Notice: Subject to any disclaimer, the term of this patent is extended or adjusted under 35 U.S.C. 154(b) by 0 days.

(21) Appl. No.: 13/514,197

(22) PCT Filed: Dec. 7, 2010

(86) PCT No.: PCT/JP2010/071892
§ 371 (c)(1),
(2), (4) Date: Jun. 6, 2012

(87) PCT Pub. No.: WO2011/074443
PCT Pub. Date: Jun. 23, 2011

(65) Prior Publication Data
US 2012/0240694 A1    Sep. 27, 2012

(30) Foreign Application Priority Data
Dec. 16, 2009    (JP) .................. 2009-284980

(51) Int. Cl.
*F16C 1/06*    (2006.01)
(52) U.S. Cl.
USPC .............................. 464/23; 464/52
(58) Field of Classification Search
USPC ............... 464/7, 23, 52, 53, 57–60; 74/500.5–502.6
See application file for complete search history.

(56) References Cited

U.S. PATENT DOCUMENTS

| | | | |
|---|---|---|---|
| 2009/0076319 A1 | | 3/2009 | Muyari |
| 2009/0143642 A1 | * | 6/2009 | Takahashi et al. |
| 2011/0138962 A1 | | 6/2011 | Ozaki et al. |

FOREIGN PATENT DOCUMENTS

| | | | |
|---|---|---|---|
| FR | 674435 | * | 1/1930 |
| FR | 2363724 | * | 5/1978 |
| JP | 53-035336 | | 3/1978 |
| JP | 54-180854 | | 12/1979 |
| JP | 55-008214 | | 1/1980 |
| JP | 08-067258 | | 3/1996 |
| JP | 10-019860 | | 1/1998 |
| JP | 2001-330032 | | 11/2001 |
| JP | 2004-232767 | | 8/2004 |
| JP | 2007-050752 | | 3/2007 |
| JP | 2007050752 | * | 3/2007 |
| JP | 2008-223832 | | 9/2008 |

(Continued)

OTHER PUBLICATIONS

International Search Report of Corresponding PCT Application PCT/JP2010/071892 mailed Jan. 18, 2011.
English Translation of the International Preliminary Report on Patentability mailed Jul. 19, 2012 issued in corresponding International Patent Application No. PCT/JP2010/071892.

(Continued)

*Primary Examiner* — Gregory Binda
*Assistant Examiner* — Josh Skroupa

(57) ABSTRACT

A flexible wire assembly of a compact structure that can transmit the torque for a high speed rotation even in a bent condition is provided. The flexible wire assembly includes a flexible outer tube, in which a flexible inner wire having its opposite ends defining rotation input and output ends, respectively, is rotatably supported by means of a plurality of rolling bearings. Spring elements are employed for applying preloads to those rolling bearings. The use is also made of a speed reducing mechanism for reducing in speed and outputting rotation of the inner wire. The spring elements include inner ring spring elements and outer ring spring elements that are alternately arranged over the length of the inner wire.

11 Claims, 10 Drawing Sheets

(56) References Cited

FOREIGN PATENT DOCUMENTS

| | | |
|---|---|---|
| JP | 2009-072215 | 4/2009 |
| JP | 2009-222163 | 10/2009 |
| WO | WO 2010/018665 | 2/2010 |

OTHER PUBLICATIONS

Japanese Office Action for corresponding Japanese Application 2009-284980; Issued Jul. 16, 2013.

* cited by examiner

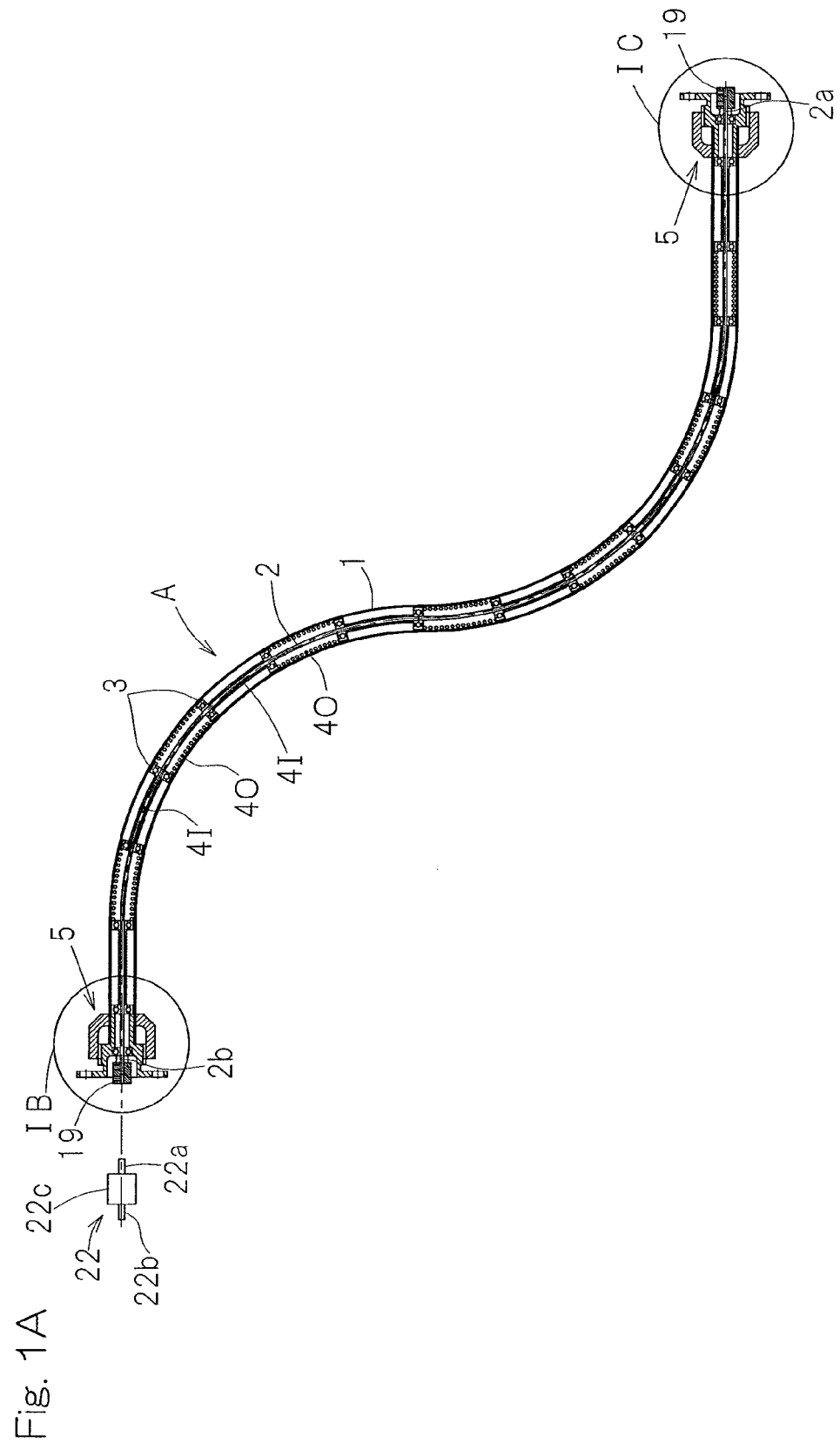

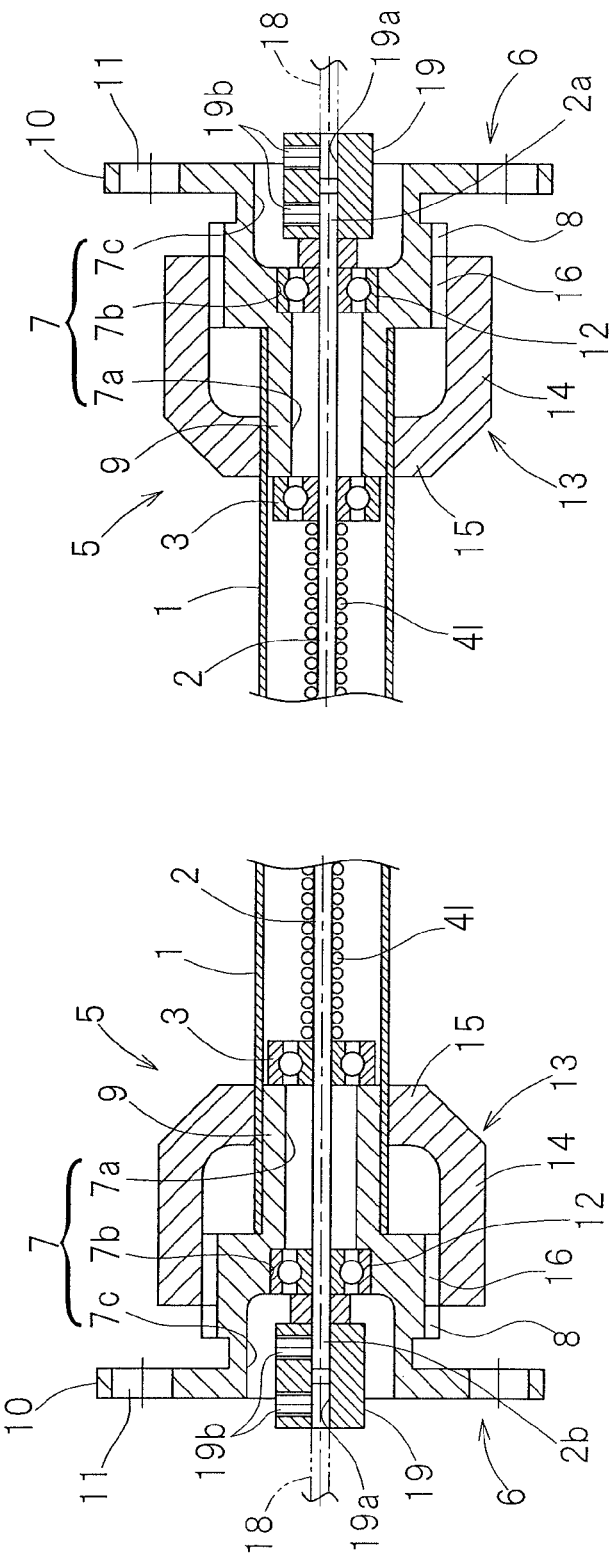

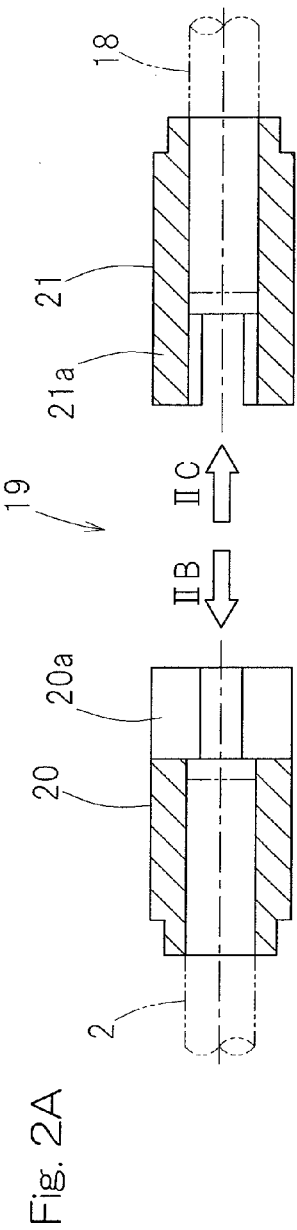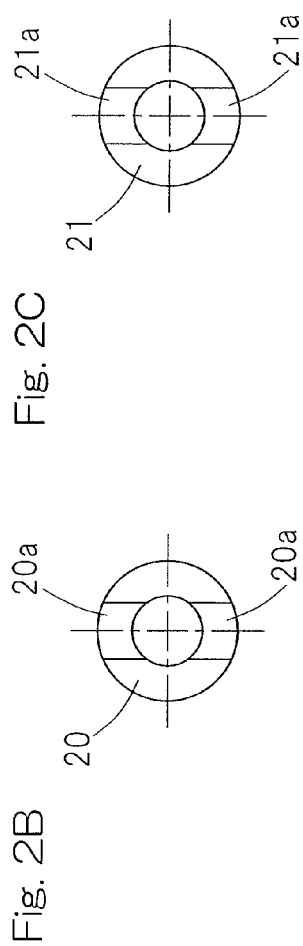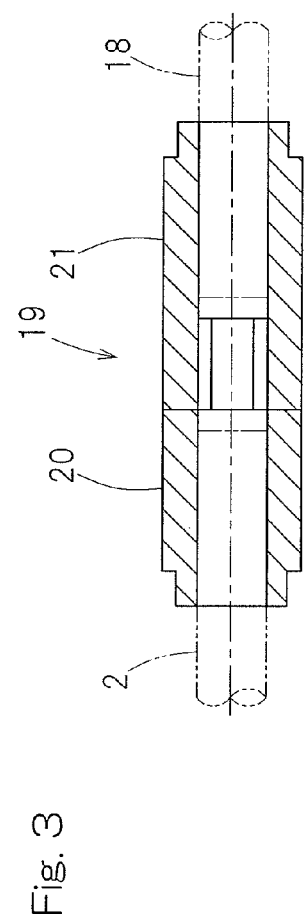

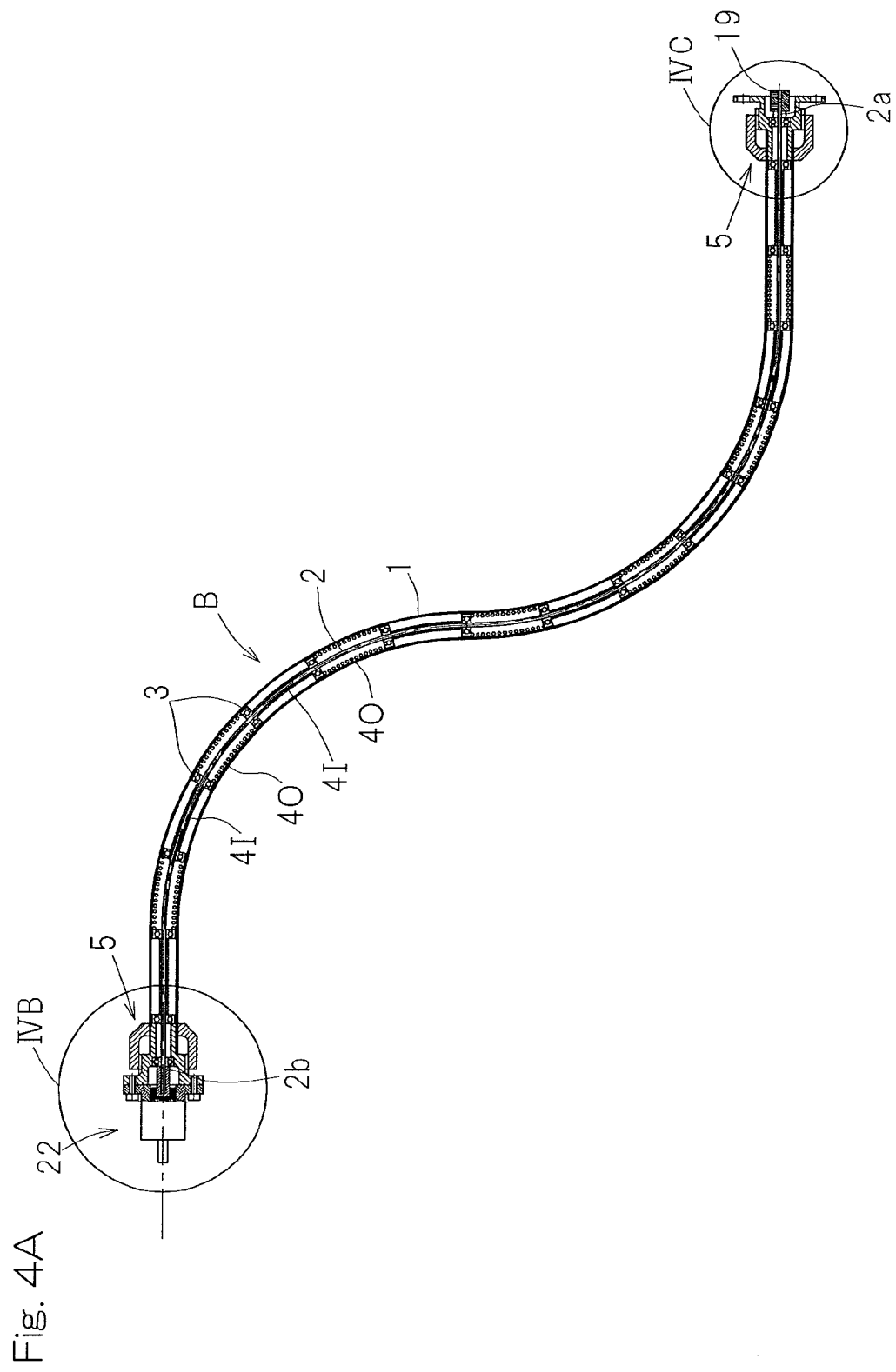

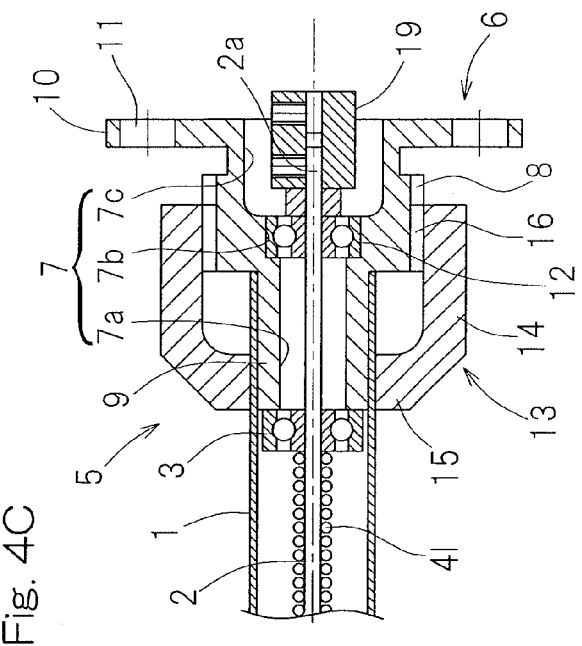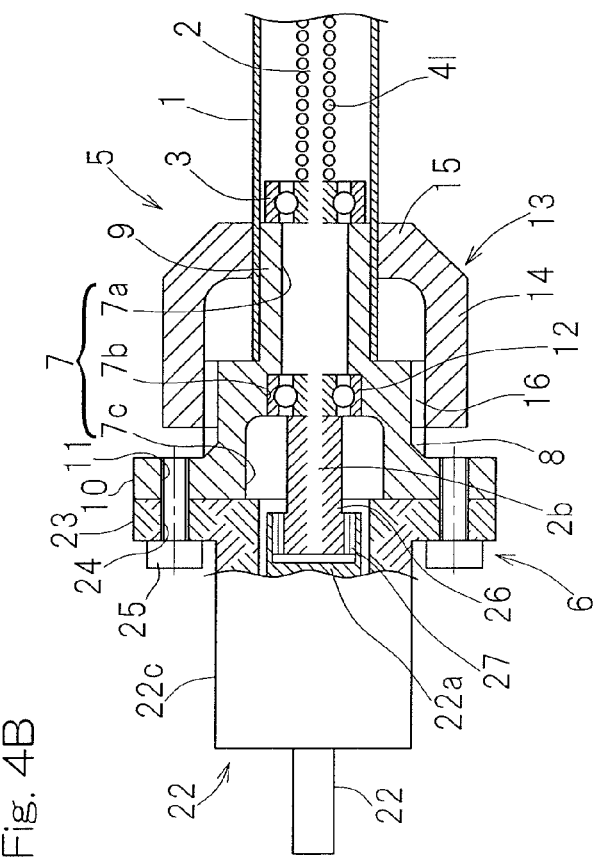

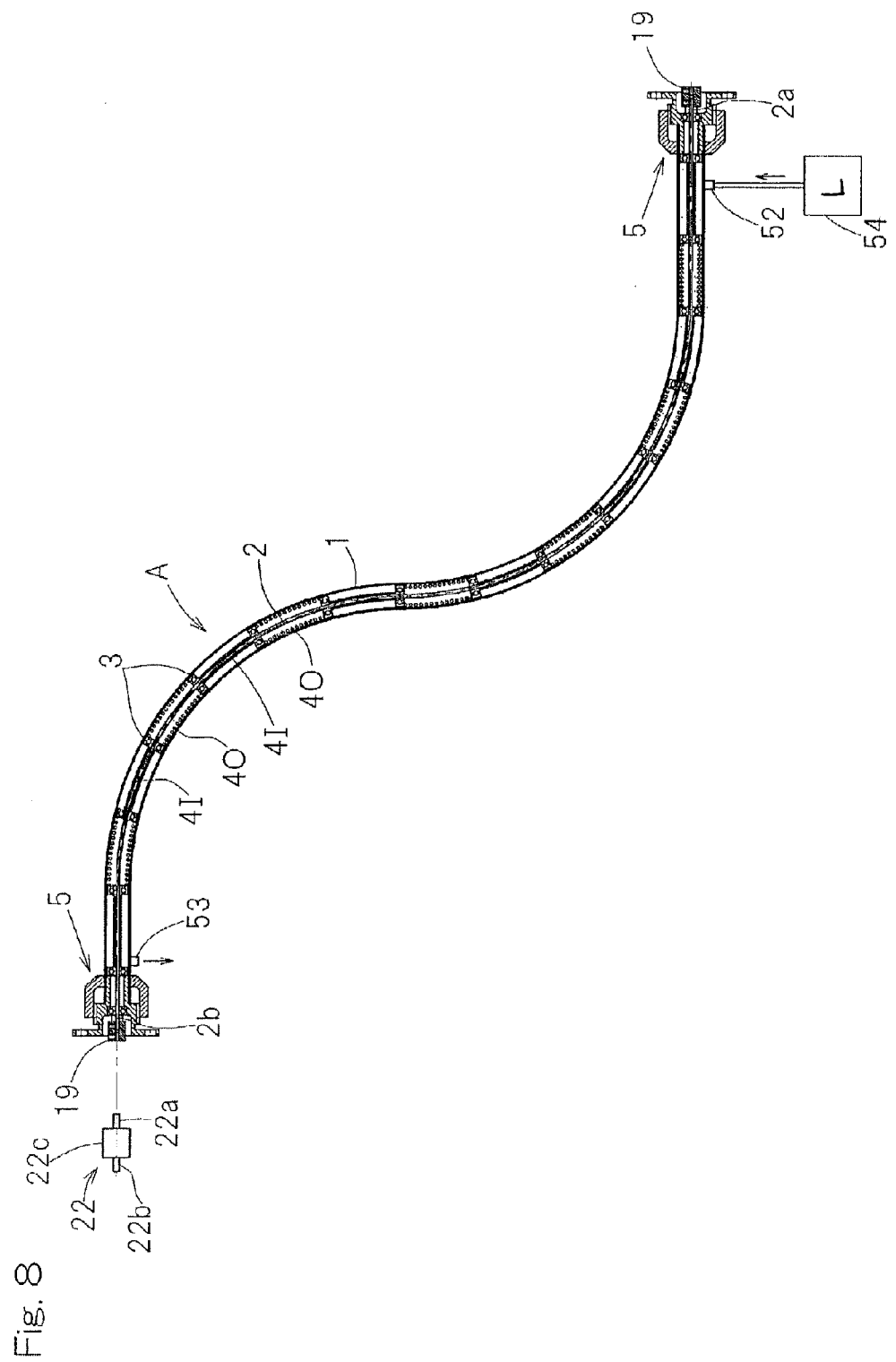

FLEXIBLE WIRE

CROSS REFERENCE TO RELATED APPLICATIONS

This application claims the benefit, under 35 U.S.C. Section 371, of PCT International Application No. PCT/JP2010/071892, filed Dec. 7, 2010, which claimed priority to Japanese Application No. 2009-284980, filed Dec. 16, 2009 in the Japanese patent office, the disclosures of which are hereby incorporated by reference.

BACKGROUND OF THE INVENTION

1. Field of the Invention

The present invention relates to a flexible wire assembly for use in a machine or equipment for medical use for transmitting a torque to a remote controlled actuating machine or equipment.

2. Description of Related Art

For remote control of a working device positioned at a distant location, a flexible power transmitting device is utilized for transmitting a power of a drive source, mainly a torque, to the actuating equipment such as disclosed in the patent documents 1 and 2 listed below.

The power transmitting device disclosed in the patent document 1 referred to above is of a type provided in an inspection probe device and is so designed as to include a flexible shaft for transmitting the torque, which is transmitted from a rotating drive source in the form of an electric motor through a slip ring, to a inspection probe, a plurality of bearings arranged on an outer periphery of the flexible shaft and axially spaced from each other at intervals of a predetermined distance, and a coiled spring functioning as a protective tube enclosing the flexible shaft and the bearings.

The power transmitting device disclosed in the patent document 2 referred to above is of a type provided in an endoscopic treating instrument and is so designed as to include a wire having its tip fitted with a treating member, a flexible tubular member having a hollow in which the wire is inserted, and bearings for supporting the wire in a fashion rotatable relative to the tubular member.

The patent document 3 listed below discloses the use of a flexible shaft connected with an output side, but the details of the flexible shaft are unspecified.

PRIOR ART DOCUMENTS

[Patent Document 1] JP Laid-open Patent Publication No. H10-19860
[Patent Document 2] JP Laid-open Patent Publication No. 2009-72215
[Patent Document 3] JP Laid-open Patent Publication No. 2004-232767

SUMMARY OF THE INVENTION

The power transmitting device disclosed in any one of the patent documents 1 and 2 listed above is such that no preload is applied to the bearings used to support the flexible shaft or the flexible wire assembly. For this reason, it is suspected that the flexible shaft or the flexible wire assembly has the natural frequency that is low to such an extent that the flexible shaft or the flexible wire assembly can no longer be driven at a high speed.

In the case of the wire, the need is recognized that the wire need to be thinned in order for it to have a sufficient flexibility. However, since the thin wire has a low torsional strength, such thin wire is unable to transmit a large torque. In addition, under the influence of torsion, a difference in rotational phase tends to occur between input and outsides and, therefore, it is difficult to control the angle of rotation.

In view of the foregoing, the present invention has for its object to provide a flexible wire assembly of a compact structure that can transmit the torque for a high speed rotation even in a bent condition.

In order to accomplish the foregoing object, the present invention provides a flexible wire assembly which includes: a flexible outer tube; a flexible inner wire rotatably extending in the flexible outer tube and having an input end of rotation and an output end of rotation opposite to each other; a plurality of rolling bearings for rotatably supporting the flexible inner wire; spring elements interposed between the neighboring rolling bearings for applying respective preloads to the rolling bearings; and a speed reducing mechanism drivingly connected with the rotation output end of the inner wire for reducing the speed of the rotation of the inner wire and outputting the rotation of the inner wire.

According to the structure, because of the use of the speed reducing mechanism for reducing the rotational speed of the inner wire and outputting it, the flexible wire assembly of the structure hereinabove described can provide a high torque even though the torque to be transmitted through the inner wire is low. When the torque to be transmitted through the inner wire is low, a thin wire may be employed for the inner wire. For this reason, the flexible wire assembly having a high flexibility can be realized with a compact structure. Also, because of the provision of the spring elements interposed between the neighboring rolling bearings for applying the preloads to those rolling bearings, any possible lowering of the natural frequency of the inner wire can be suppressed and the inner wire can be rotated at a high speed.

The spring elements referred to above may include an inner ring spring element for applying the preload to an inner ring of each of the rolling elements and an outer ring spring element for applying the preload to an outer ring of each of the rolling elements. Those inner and outer ring spring elements are in this case arranged within the outer tube alternately in a direction lengthwise of the outer tube. The alternate positioning of the inner ring spring element and the outer ring spring element over the length of the inner wire makes it possible to use the spring elements with no need to increase the diameter of the outer tube.

In one embodiment of the present invention, a rotary drive source may be drivingly connected with the rotation input end of the inner wire for driving the inner wire. The use of the rotary drive source makes it possible to apply the torque efficiently to the inner wire.

In another embodiment of the present invention, a rotary mechanism may be provided on an output side of the speed reducing mechanism for rotatably driving a terminal output unit with a rotary output, the speed of which has been reduced by the speed reducing mechanism. Alternatively, a linear motion mechanism may be disposed on an output side of the speed reducing mechanism for translating a rotary output, the speed of which has been reduced by the speed reducing mechanism, into a linear motion mechanism and then causing a terminal output unit to undergo the linear motion.

As hereinbefore described, the flexible wire assembly is capable of generating a high torque when provided with the speed reducing mechanism. For this reason, where the rotary drive mechanism is employed on the output side of the speed reducing mechanism, the terminal output unit of the rotary drive mechanism can be rotated with a high torque, but where the linear motion mechanism is employed on such output side, the terminal output unit of this linear motion mechanism can be actuated with the large thrust force. In addition, since a force necessary to overcome the friction occurring in the linear motion mechanism is generated, a stick slip will hardly occur even though the torsional rigidity of the inner wire is low.

In the case that either the rotary drive mechanism or the linear motion mechanism is employed in association with the flexible wire assembly of the structure described above, a position detecting unit may be employed for detecting the operational position of the rotary mechanism or the linear motion mechanism.

The use of the position detecting unit makes it possible to accomplish a feedback control with an output value of such position detecting unit and, therefore, the positioning accuracy relative to an object to be controlled at a distant place such as, for example, an actuating machine or equipment can be increased. Also, since the rotation of the inner wire is reduced in speed and outputted by the speed reducing mechanism and since influences brought about by twisting of the inner wire appearing in the rotary mechanism or the linear motion mechanism is minimized, not only can the positioning resolution be maintained at a high level, but a highly accurate feedback control can also be accomplished.

In a further embodiment of the present invention, a joint member may be provided at opposite ends of or one of the opposite ends of the outer tube for detachably connecting the outer tube with any other member. The use of the joint member this way is effective to connect the flexible wire assembly of the present invention with any other member easily.

In a still further embodiment of the present invention, the joint member may include a tubular male screw member having an inner periphery formed with a throughhole for passage of the inner wire therethrough and also having an outer periphery formed with an externally threaded portion, the tubular male screw member having a first axial end received within the outer tube, and a tubular female screw member having an inner periphery formed with an internally threaded portion threadingly engageable with the externally threaded portion and also having a first end mounted on an outer diametric portion of the outer tube. In this case, the use is preferred of a coupling member in one of the male screw member and the female screw member for connecting it with any other member.

Where the joint member is employed, when in a condition in which the first axial end of the male screw member is engaged in an inner diametric portion of the outer tube and the first axial end of the female screw member is engaged in an outer diametric portion of the outer tube, the externally threaded portion of the male screw member is engaged with the internally threaded portion of the female screw member, the respective first axial ends of the male and female screw members sandwich and fix the outer tube from opposite directions. Then, a connecting means provided in either one of the male screw member or the female screw member is connected with any other member which forms an object to be connected. Accordingly, the outer tube and the other member are connected together.

However, when the male and female screw members are disengaged from each other, the outer tube is released from the respective first axial ends of the male and female screw members and the connection between the outer tube and the other member are therefore released. In any event, the connection of the outer tube with the other member and the disengagement of the outer tube from the other member can be easily accomplished one at a time. Also, in a condition in which the outer tube and the joint member are connected together, the connection of the outer tube with the other member and the disengagement of the outer tube from the other member are carried out by means of the connecting means of the male screw member. Hence, the connection of the outer tube with the other member and the disengagement of the outer tube from the other member can be accomplished easily.

In a yet further embodiment of the present invention, a coupling element may be provided at opposite ends of or one of the opposite ends of the inner wire for connecting it with a rotary shaft that is rotatably supported in face to face relation with the opposite ends or one of the opposite ends of the inner wire. The use of the coupling element is effective to facilitate connection of the inner wire with the rotary shaft.

The coupling element referred to above is comprised of a wire side member rotatable together with the inner wire and a shaft side member rotatable together with the rotary shaft. The wire side member and the shaft side member have respective mating end faces that confront each other when the wire side member and the shaft side member are connected together. One of the mating end faces has a radially extending groove defined therein while the other of the mating end faces has an axially extending projection defined therein and engageable in the radially extending groove. Accordingly, when the wire side member and the shaft side member are connected together with the axially extending projection engaged in the radially extending groove, the inner wire and the rotary shaft are drivingly connected with each other.

According to the peculiar configuration of the coupling element as hereinabove described, when the inner wire and the rotary shaft are to be connected with each other, the wire side member and the shaft side member, disposed in face to face relation to each other, are to be relatively moved close towards each other in a direction axially of the coupling element until the radially extending groove receives therein the axially extending projection. To release the connection between the inner wire and the rotary shaft, the wire side member and the shaft side member are to be relatively moved in respective directions away from each other to thereby disengage the connection between the radially extending groove and the axially extending projection. Thus, the connection of the inner wire with the rotary shaft and the disengagement of the inner wire from the rotary shaft can be accomplished easily.

In a still yet further embodiment of the present invention, a lubricant may be filled in or be allowed to flow through the rolling bearings within the outer tube. If the lubricant is filled or is allowed to flow through the rolling bearings within the outer tube, the rolling performances of those rolling bearings can be maintained at a high level.

BRIEF DESCRIPTION OF THE DRAWINGS

In any event, the present invention will become more clearly understood from the following description of embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 1A is a sectional view of a flexible wire assembly designed in accordance with a first embodiment;

FIG. 1B is a diagram showing, on an enlarged scale, a portion indicated by IB in FIG. 1A;

FIG. 1C is a diagram showing, on an enlarged scale, a portion indicated by IC in FIG. 1A;

FIG. 2A is a sectional view showing the flexible wire assembly having its coupling elements held in a separated condition;

FIG. 2B is an end view of one of the coupling elements as viewed in a direction of the arrow IIB in FIG. 2A;

FIG. 2C is an end view of one of the coupling elements as viewed in a direction of the arrow IIC in FIG. 2A;

FIG. 3 is a sectional view showing the coupling elements in a connected condition;

FIG. 4A is a sectional view of the flexible wire assembly designed in accordance with a second embodiment;

FIG. 4B is a diagram showing, on an enlarged scale, a portion indicated by IVB in FIG. 4A;

FIG. 4C is a diagram showing, on an enlarged scale, a portion indicated by IVC in FIG. 4A;

FIG. 8 is a sectional view showing the flexible wire assembly designed in accordance with a fourth embodiment.

DESCRIPTION OF THE PREFERRED EMBODIMENTS

Figure 5:
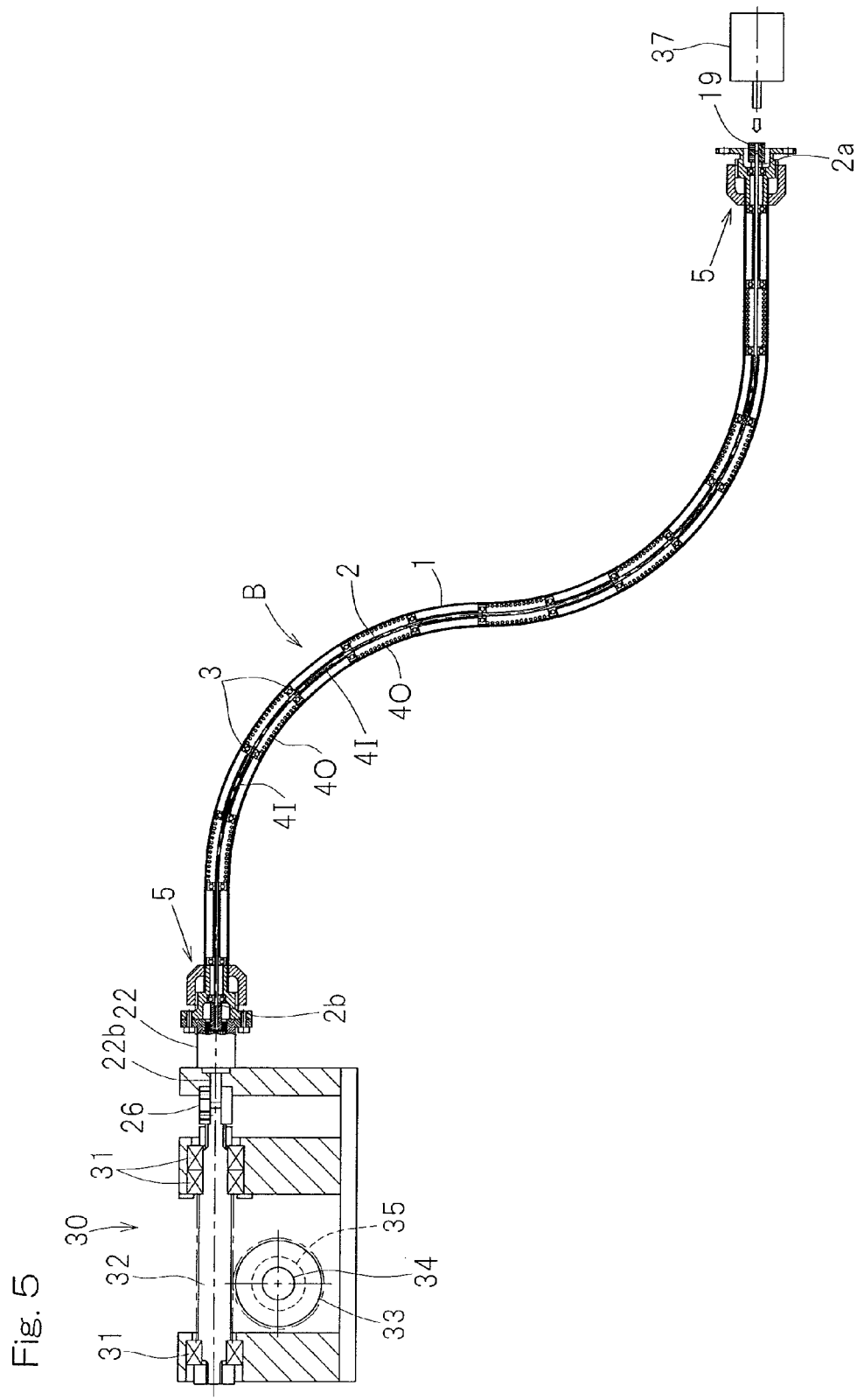
FIG. 5 is a sectional view showing an example of use of the flexible wire assembly designed according to the embodiments.

A first embodiment of the present invention is shown in FIGS. 1A to 1C. A flexible wire assembly A shown therein includes a flexible outer tube 1, a flexible inner wire 2 provided within the outer tube 1 so as to extend along a center line thereof, and a plurality of rolling bearings 3 for supporting the inner wire 2 in a fashion rotatable relative to the outer tube 1. The inner wire 2 has its opposite, first and second ends defining a rotation input end 2a and a rotation output end 2b, respectively. A speed reducing mechanism 22 as will be detailed later is provided on one side adjacent the output end 2b of the inner wire 2. The outer tube 1 is made of, for example, a resinous material. As a material for the inner wire 2, however, metal, resin or glass fibers, for example, may be employed. This inner wire 2 may be either a single wire or a twisted wire.

The rolling bearings 3 are positioned within the outer tube 1 and are spaced a predetermined distance from each other along the center line of the outer tube 1, and spring elements 4I and 4O for applying respective preloads to those rolling bearings 3 are provided between the neighboring rolling bearings 3. The spring elements 4I and 4O are employed in the form of, for example, coiled compression springs and are provided so as to allow the winding to enclose an outer periphery of the inner wire 2. The spring elements includes an inner ring spring element 4I for causing a preload to be developed in respective inner rings of the rolling bearings 3 and an outer ring spring element 4O for causing a preload to be developed in respective outer rings of the rolling bearings 3, and those spring elements 4I and 4O are disposed alternately with each other.

The outer tube 1 has its opposite, first and second ends provided with first and second joint members 5, respectively, that are used to connect the outer tube 1 with other component parts. The joint member 5 is comprised of a male screw member 6 and a female screw member 13. The male screw member 6 is a tubular member having its inner periphery formed with a throughhole 7 and an externally threaded portion 8 is formed on an outer peripheral portion of an axial intermediate portion thereof. The male screw member 6 has a first axially oriented end provided with a cylindrical portion 9 extending in a direction axially of the male screw member 6 and having a constant inner diameter and a constant outer diameter. The outer diameter of the cylindrical portion 9 is so chosen that the cylindrical portion 9 can be snugly and neatly inserted into the corresponding end of the outer tube 1. The male screw member 6 has a second axially oriented end, opposite to the first axially oriented end referred to above, which is provided with a radially outwardly extending flange portion 10. The flange portion 10 forms a connecting member for the connection with an external component part and is formed with insertion holes 11 defined therein at a plurality of locations for the passage of corresponding fixing members such as, for example, bolts. It is to be noted that each of the throughholes 7 refereed to previously is comprised of a small diameter portion 7a, an middle diameter portion 7b and a large diameter portion 7c, having its inner diameter increasing stepwise from one end thereof adjacent the cylindrical portion 9 towards the opposite end thereof adjacent the flange portion 10. The middle diameter portion 7b accommodates therein a rolling bearing 12 inserted therein under interference fit for rotatably supporting the inner wire 2.

The female screw member 13 is a tubular member comprised of a cylindrical shaped portion 14 and a collar portion 15 extending radially inwardly from one end of the cylindrical shaped portion 14 remote from the flange portion 10, and that end of the cylindrical shaped portion 14 adjacent the flange portion 10 has an inner peripheral portion formed with an internally threaded portion 16 that is engageable with the externally threaded portion 8 defined in an outer peripheral portion of the male screw member 6. The collar portion 15 has an inner diameter so chosen that an outer peripheral surface of the outer tube 1 can be snugly and neatly engaged therein.

When the outer tube 1 is connected with the external component part, the cylindrical portion 9 of the male screw member 6 is engaged in an inner diameter portion of the outer tube 1 with the collar portion 15 of the female screw member 13 being snugly and neatly seated on an outer diametric portion of the outer tube 1, followed by engagement of the male screw member 6 with the female screw member 13, by allowing the externally threaded portion 8 of the male screw member 6 to be threadingly engaged with the internally threaded portion of the female screw member 13. By so doing, that first end of the outer tube 1 can be held in position on the outer periphery of the cylindrical portion 9 as radially sandwiched between the cylindrical portion 9 and the collar portion 15 of the female screw member 13. At this time, the inner wire 2 is allowed to extend axially outwardly from the throughhole 7 and is then rotatably supported by the rolling bearing 12 inserted in the middle diameter portion 7b of the throughhole 7. Subsequently, the flange portion 10 of the male screw member 6 is connected with the external component part (not shown), which is an object to be connected with the flange portion 10. The connection of the flange portion 10 with the external component part is accomplished by the use of the fixing members (not shown), for example, the bolts inserted through the respective insertion holes 11, thereby completing the connection of the outer tube 1 with the external component part as shown in FIGS. 1A to 1C.

If starting from the condition described above, the threaded engagement of the externally threaded portion 8 with the internally threaded portion 16 is released in a manner reverse to the connection therebetween, the outer tube 1 can be released from the constraint by the cylindrical portion 9 of the male screw member 6 and the collar portion 15 of the female screw member 13, thus releasing the connection between the outer tube 1 and the object to be connected therewith. The release of the outer tube 1 from the external component part and other releasing operations can be accomplished easily. It is to be noted that the release and connection between the flexible wire assembly A and any other member may be performed by means of the connecting member (flange portion 10) of the male screw member 6 with the outer tube 1 and the joint member 5 being connected together. In this way, the connection and release between the flexible wire assembly A and the other member can also be accomplished further easily.

Both of the rotation input and output ends 2a and 2b of the inner wire 2 are provided with coupling elements 19 for connection with respective rotary shafts 18 such as, for example, input and output shafts. Each of the coupling elements 19 shown has an axially extending throughhole 19a defined therein, and has two axially spaced screw holes 19b defined therein so as to extend between an outer periphery of the respective coupling element 19 and the throughhole 19a. The inner wire 2 and the associated rotary shaft 18 can be firmly secured to the respective coupling element 19 to connect the inner wire 2 and the rotary shaft 18 together when corresponding screw members (not shown) such as, for example, bolts then threadingly engaged in the associated screw holes 19b are fastened against the inner wire 2 and the rotary shaft 18.

The coupling element 19 referred to above and employed respectively at the first and second joint members 5 may be of any other suitable structure, provided that the inner wire 2 and the rotary shaft 18 may be connected with each other for rotation together. By way of example, each of the coupling elements 19 may be so designed and so configured as shown in FIGS. 2A to 2C and 3. Referring now to FIGS. 2A to 2C, each of the coupling elements 19 includes a wire side member 20, rotatable together with the inner wire 2, and a shaft side member 21 rotatable together with the rotary shaft 18. The wire side member 20 and the inner wire 2, as well as the shaft side member 21 and the rotary shaft 18, are firmly connected together either under interference fit or by means of respective suitable fixing members (not shown) such as bolts. The wire side member 20 and the shaft side member 21 have respective mating end faces, and the mating end face of the wire side member 20 is formed with a radially extending groove 20a whereas the mating end face of the shaft side member 21 is formed with an axially protruding projection 21a engageable in the radially extending groove 20a. In the example shown in FIGS. 2A to 2C, the radial groove 20a is defined in the wire side member 20 at two locations spaced an angular distance from each other in a direction circumferentially thereof and the axially extending projection 21a is defined in the shaft side member 21 at correspondingly two locations spaced a similar angular distance from each other in a direction circumferentially thereof.

To connect the inner wire 2 and the rotary shaft 18 together, the wire side member 20 and the shaft side member 21 have to be axially moved in a direction relatively towards each other as shown in FIG. 2A, followed by insertion of the axially extending projection 21a into the radial groove 20a as shown in FIG. 3. By so doing, the wire side member 20 and the shaft side member 21 can be connected with each other for transmission of a torque therethrough. On the other hand, to release the inner wire 2 relatively from the rotary shaft 18, the wire side member 20 and the shaft side member 21 have to be relatively moved in the axial direction in a manner reverse to that described above, to thereby separate them from each other, followed by disengagement of the projection 21a from the radial groove 20a. In any event, connection and release between the inner wire 2 and the rotary shaft 18 can be easily accomplished.

The output side of the flexible wire assembly A is provided with a speed reducing mechanism 22 for reducing the rotational speed, that is, the number of revolutions of the inner wire 2. The speed reducing mechanism 22 is of a design, in which input and output shafts 22a and 22b protruding from a speed reducing mechanism housing 22c in opposite directions are rotatably supported and a rotation reducing and transmitting system (not shown) for reducing the rotational speed of the input shaft 22a and then transmitting to the output shaft 22b is provided within the speed reducing mechanism housing 22c. In the example as shown, the input shaft 22a and the output shaft 22b are disposed on the same axis, i.e., axially aligned with each other. For the rotation reducing and transmitting system for the speed reducing mechanism 22 as hereinabove mentioned, a planetary gear mechanism or a harmonic drive gearing, for example, may be employed. The input shaft 22a of the speed reducing mechanism 22 is connected with the rotary shaft 18 that is connected with the output side of the inner wire 2 through the coupling element 19. On the other hand, the output shaft 22b of the speed reducing mechanism 22 is connected with an external actuating instrument (not shown).

The flexible wire assembly A of the structure hereinabove described can provide a high torque even though the torque to be transmitted through the inner wire 2 is low, because the speed reducing mechanism 22 for reducing and then outputting the rotational speed of the inner wire 2 is provided on the output side of the inner wire 2. If the torque to be transmitted through the inner wire 2 is low, a thin wire may be employed for the inner wire 2. For this reason, the flexible wire assembly A having a high flexibility can be realized with a compact structure. Also, the use of the spring elements 4I and 4O for applying the preloads to the rolling bearings 3 disposed between the neighboring rolling bearings 3, 3 is effective to refrain the natural frequency of the inner wire 2 from being lowered, making it possible for the inner wire 2 to be rotatably driven at a high speed. Since the inner ring spring elements 4I and the outer ring spring elements 4O are alternately disposed in the longitudinal direction of the inner wire 2, the spring elements 4I and 4O can be provided with no need to increase the diameter of the outer tube 1.

FIGS. 4A to 4C illustrate a second embodiment of the present invention. In this second embodiment shown therein, the flexible wire assembly B is so designed that the joint member 5 on the output side is connected directly with the speed reducing mechanism 22. The speed reducing mechanism 22 includes a flange portion 23 integral with the speed reducing mechanism housing 22c, which flange portion 23 is formed with a plurality of insertion holes 24 alignable with the insertion holes 11 in the joint member 5 for receiving the respective fixing members. It is to be noted that each of the insertion hole 11 defined in the joint member 5 has a threaded portion defined therein. Accordingly, when while the flange portion 10 in the joint member 5 and the flange portion 23 in the speed reducing mechanism 22 are held in contact with each other with the insertion holes 24 of the flange portion 23 aligned axially with the insertion holes 11 of the flange portion 10, bolts 25 are successively inserted from the side of the speed reducing mechanism 22 into the insertion holes 24 and are then firmly threaded into the internally threaded insertion holes 11, the joint member 5 and the speed reducing mechanism 22 can be connected together.

Also, the flexible wire assembly B is such that the output end 2b of the inner wire 2 is connected directly with the input shaft 22a of the speed reducing mechanism 22. For this purpose, the rotation output end 2b of the inner wire 2 is provided with a gear 26 in place of the coupling element 19, which has been shown and described as employed in the practice of the previously described first embodiment, which gear 26 is meshed with a gear 27 provided in the input shaft 22a. In this example, the gear 26 is employed in the form of an external gear whereas the gear 27 is employed in the form of an internal gear.

The flexible wire assembly B of the foregoing structure designed according to the second embodiment is used in practice with the speed reducing mechanism 2 connected with an external member. Nothing is specifically limited in accomplishing the connection between the speed reducing mechanism 22 and the external member. According to the second embodiment of the present invention, since the number of component parts employed can be reduced, the flexible wire assembly B in its entirety can be compactized. Other than it, the flexible wire assembly B is similar in structure to that of the flexible wire assembly A in the previously described first embodiment. It is, however, to be noted that although the male screw member 6 of the joint member 5 and the speed reducing mechanism 2 have been shown and described as comprised of members separate from each other, the speed reducing mechanism 22 and the male screw member 6 may be integrated together. More specifically, the speed reducing mechanism housing 22c may be provided with the externally threaded portion 8 and the cylindrical portion 9.

One example of use of the flexible wire assembly designed in accordance with the foregoing embodiments is best shown in FIG. 5. The example of use shown in FIGS. 4A to 4C illustrates the flexible wire assembly B used to control, by remote control, a rotary mechanism 30 having a terminal output unit being a rotary unit. The rotary mechanism 30 includes a worm gear 32 having its opposite end supported by bearings 31, a worm wheel 33 meshed with the worm gear 32, a rotary shaft 34 as the terminal output unit supporting the worm wheel 33, and a rotary encoder 35, which is a position detecting unit for detecting the angle of rotation of the worm wheel 33. The output shaft 22b of the speed reducing mechanism 22 in the flexible wire assembly B is drivingly connected with one end of the opposite ends of the work gear 32 through a coupling 36. The rotary shaft 34 may be coupled directly or indirectly with working devices such as a power tool or a measuring device.

On the other hand, the rotation input end 2a of the inner wire 2 is drivingly connected with a rotary drive source 37, which is controlled by a control device (not shown), through the coupling element 19 so that the inner wire 2 can be rotatably driven by the rotary drive source 37. The torque of the inner wire 2 is transmitted to the rotary mechanism 30 after having been reduced in rotational speed thereof by the speed reducing mechanism 22, to thereby rotate the drive shaft 34. Since the use of the speed reducing mechanism 22 enables a high torque to be generated, the rotary shaft 34 can be driven with a high torque. Also, since a force necessary to overcome the friction occurring in the rotary mechanism 30 is generated, a stick slip will hardly occur even though the torsional rigidity of the inner wire 2 is low.

Figure 6:
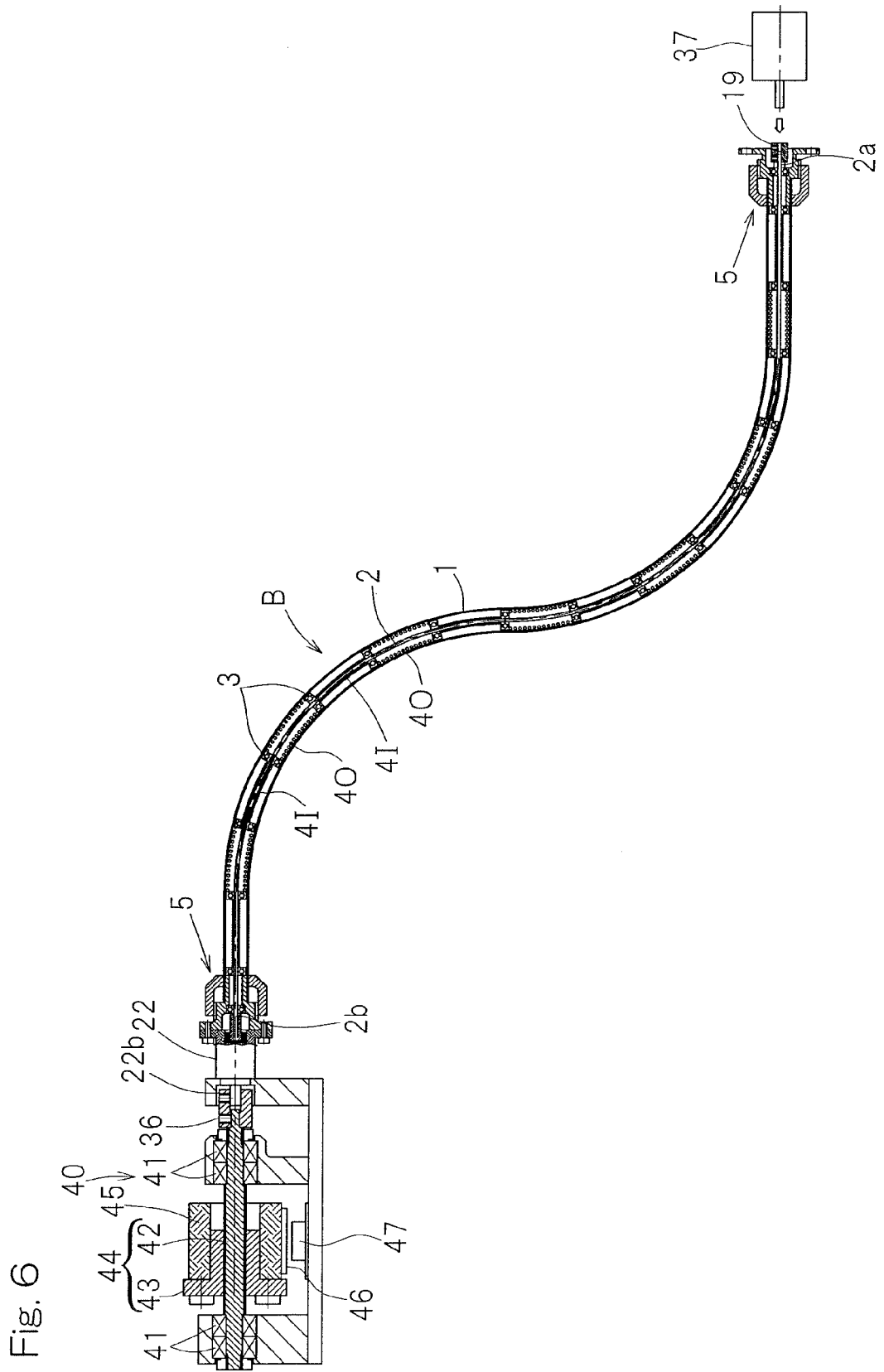
FIG. 6 is a sectional view showing another example of use of the flexible wire assembly designed according to the embodiments.

FIG. 6 illustrates a different example of use of the flexible wire assembly. According to the example of use shown in FIG. 6, the flexible wire assembly B shown in and described with reference to FIGS. 4A to 4C is used to control, by remote control, a linear motion mechanism 40 having the terminal output unit being a linear motion section. The linear motion mechanism 40 includes a ball screw mechanism 44 made up of a ball screw 42, having its opposite ends supported by bearings 41 spaced a distance from each other in a direction axially of the ball screw 42, and a nut 43 threadingly mounted on the ball screw 42, and a linear motion member 45 as the terminal output unit is fixed to the nut 43 by means of one or more bolts (not shown). By the action of the ball screw mechanism 44, a rotary motion of the ball screw 42 is translated into a linear motion and, therefore, the linear motion member 45 is linearly moved in the direction axially of the ball screw 42. A linear scale 46 having calibrations is mounted on the linear motion member 45, and the calibrations of the linear scale 46 are read one at a time by a linear encoder 47, which is the position detecting unit. The output shaft 22b of the speed reducing mechanism 22 in the flexible wire assembly B is drivingly connected with one of the opposite ends of the ball screw 42 through a coupling 36. A working device such as, for example, a tool or a measuring device is adapted to be fitted directly or indirectly to the linear motion member 45.

The rotary drive source 37 is connected with the input side of the inner wire 2 through the coupling element 19, and the inner wire 2 is rotatably driven by this rotary drive source 37. The rotary drive source 37 is controlled by a control device (not shown). The torque of the inner wire 2 is transmitted to the linear motion mechanism 40 after having reduced in rotational speed thereof by the speed reducing mechanism 22, and the linear motion member 45 is therefore driven linearly. Since the use of the speed reducing mechanism 22 makes it possible to generate a high torque, a large thrust force can be obtained from the linear motion member 45. Also, since a force necessary to overcome the friction occurring in the linear motion mechanism 40 is generated, a stick slip will hardly occur even though the torsional rigidity of the inner wire 2 is low.

In controlling the rotary mechanism 30 or the linear motion mechanism 40 at a distant place, the amount of output of the rotary drive source 37 may be controlled by inputting a control command manually to the control device, but if the amount of output of the rotary drive source 37 is automatically controlled by feed an output value of the rotary encoder 35 or the linear encoder 47 back to the control device, the positioning accuracy of the instrument, which is an object to be controlled by remote control, can be increased.

Also, since the rotation of the inner wire 2 is reduced in speed by the speed reducing mechanism 22 and since influences brought about by twisting of the inner wire 2 appearing in the rotary mechanism 30 or the linear motion mechanism 40 is minimized, not only can the positioning resolution of the rotary encoder 35 or the linear encoder 47 be maintained at a high level, but a highly accurate feedback control can also be accomplished. For this reason, the rotary mechanism 30 or the linear motion mechanism 40 can be accurately controlled at a distant place.

While in describing the respective examples shown in FIGS. 5 and 6, reference has been made to the use of the flexible wire assembly B of the structure shown and described in connection with the second embodiment, the description similar thereto can be equally apply even where the flexible wire assembly A shown and described in connection with the first embodiment and, with the flexible wire assembly A, the rotary mechanism 30 or the linear motion mechanism 40 can be accurately controlled at the distant place.

Any of those flexible wire assemblies A and B can be suitably employed as a rotational force transmitting mechanism in remotely controlling the working machine or equipment not only in, for example, the medical field, but also in mechanical processing field. The use of any of those flexible wire assemblies A and B makes it possible to accomplish an accurate positioning and/or an accurate operation of the working machine or equipment.

Figure 7A:
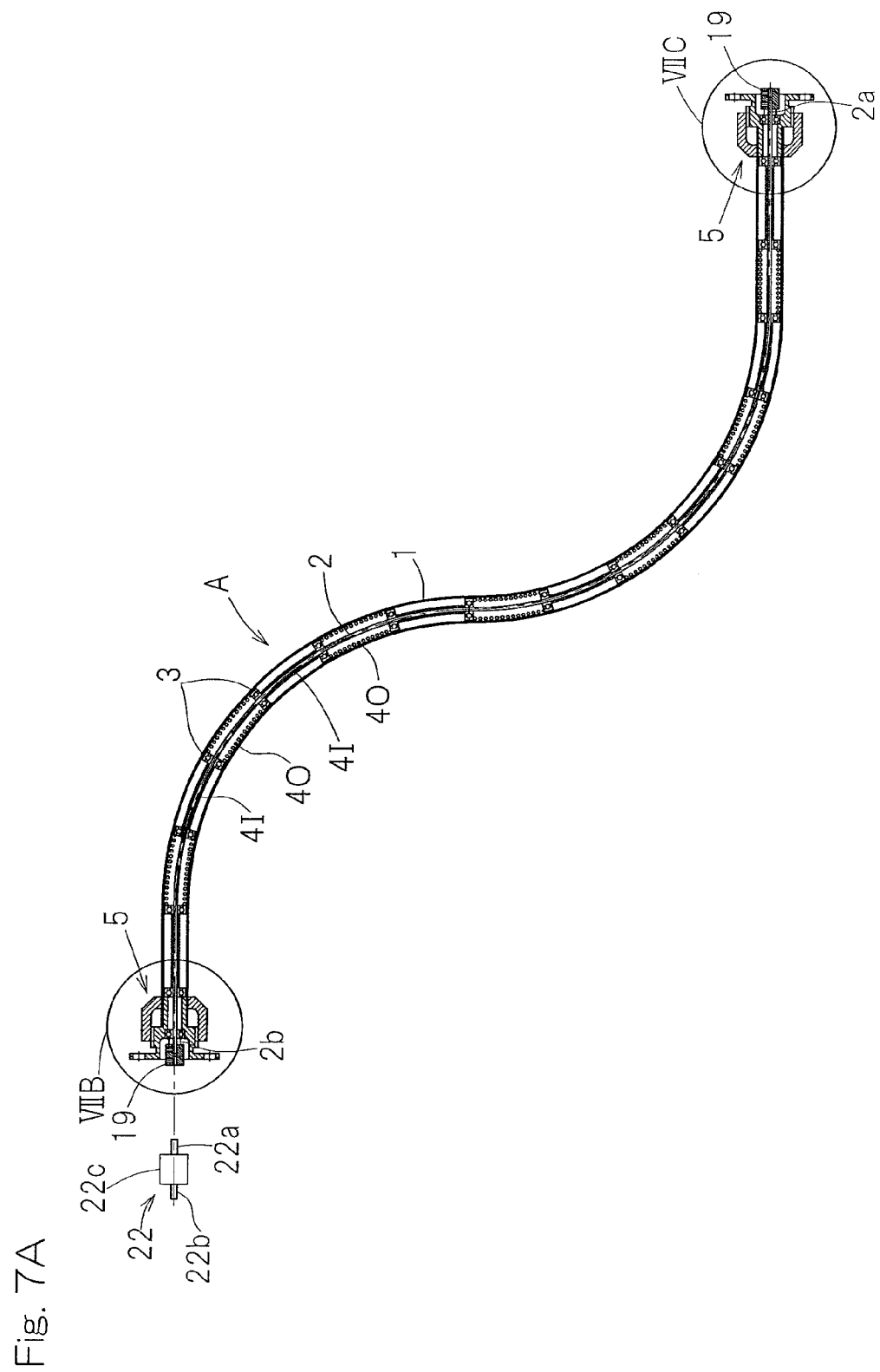
FIG. 7A is a sectional view of the flexible wire assembly designed in accordance with a third embodiment.
Figure 7B:
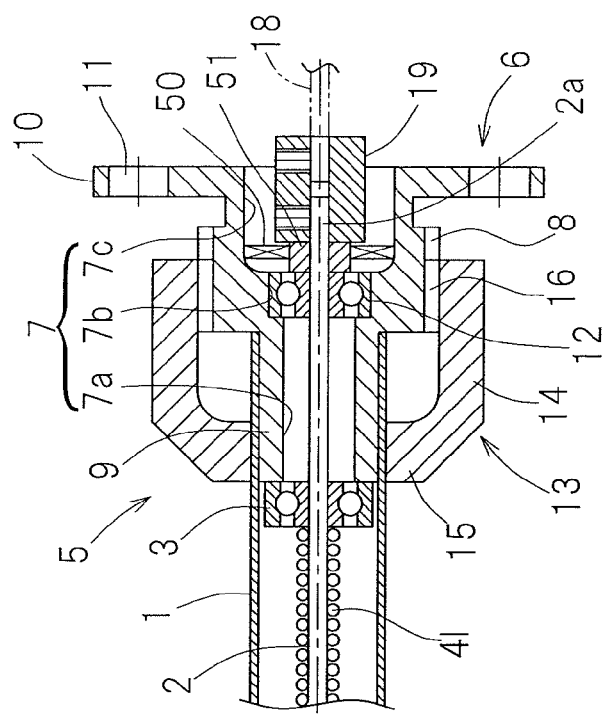
FIG. 7B is a diagram showing, on an enlarged scale, a portion indicated by VIIB in FIG. 7A.
Figure 7C:
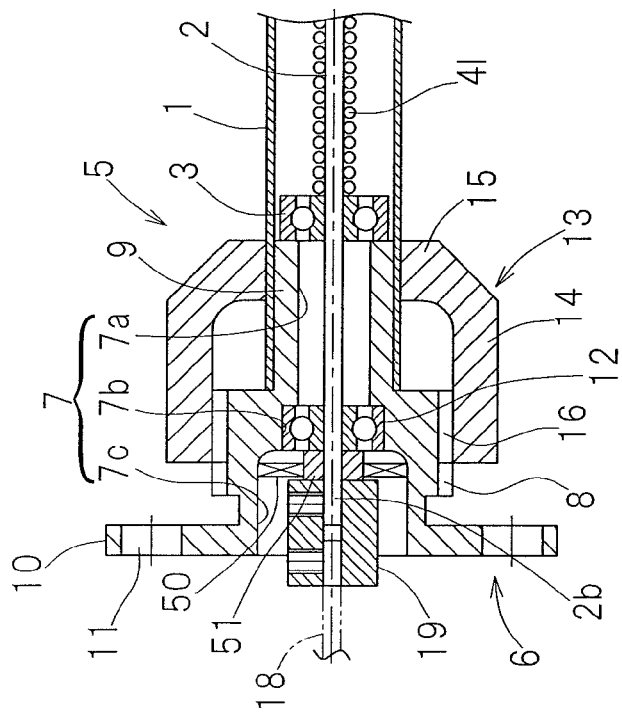
FIG. 7C is a diagram showing, on an enlarged scale, a portion indicated by VIIC in FIG. 7A.

The flexible wire assembly designed in accordance with the embodiments may have a lubricant filled in the rolling bearings 3 within the outer tube 1. FIGS. 7A to 7C illustrate a third embodiment of the present invention, in which the use is made of, for example, the flexible wire assembly A of the structure shown in and described with reference to FIGS. 1A to 1C. Referring now to FIGS. 7A to 7C, input and output side sealing members 50 are provided between the rotation input end 2a of the inner wire 2 and the adjacent joint member 5 on the input side and between the rotation output end 2b of the inner wire 2 and the adjacent joint member 5 on the output side, respectively, allowing the outer tube 1 to have a sealed structure, to avoid an undesirable leakage of the lubricant to the outside. In the example shown therein, the input side sealing member 50 is interposed between an input side tubular member 51, mounted on an outer periphery of the rotation input end 2a of the inner wire 2, and the male screw member 6 in the joint member 5 on the input side and the output side sealing member 50 is interposed between an output side tubular member 51, mounted on an outer periphery of the rotation output end 2b of the inner wire 2, and the male screw member 6 in the joint member 5 on the output side. It is, however, to be noted that in place of the use of the sealing members 50, a sealed structure may be embodied within the outer tube 1 by providing respective slide bearings (not shown) one between the rotation input end 2a of the inner wire 2 and the joint member 5 on the input side and the other between the rotation output end 2b of the inner wire 2 and the joint member 5 on the output side. For the lubricant, the use may be made of a grease of a kind having no fluidity. If the lubricant is filled in the outer tube 1 in this way, respective rolling performances of the rolling bearings 3 can be maintained at a favorable level.

FIG. 8 illustrates a fourth embodiment. In this embodiment, the lubricant L for the rolling bearings 3 is allowed to flow within the outer tube 1. Specifically, not only is the sealed structure embodied within the outer tube 1 by providing the respective sealing members (not shown), one between the rotation input end 2a of the inner wire 2 and the joint member 5 on the input side and the other between the rotation output end 2b of the inner wire 2 and the joint member 5 on the output side in a manner similar to those described hereinbefore, but a lubricant inlet 52 and a lubricant outlet 53 are also defined in the opposite, first and second ends of the outer tube 1, so that the lubricant L supplied from a lubricant supply device 54 can be introduced into the outer tube 1 through the lubricant inlet 52 and discharged outwardly from the outer tube 1 through the lubricant outlet 53. The lubricant L discharged from the lubricant outlet 53 may be recovered back to the lubricant supply device 54 for recirculation thereof through the inside of the outer tube 1. For the lubricant, the use may be made of the lubricant having a high fluidity. If the inside of the outer tube 1 is utilized as a passage for the flow of the lubricant in the manner described above, lubrication of the rolling bearings 3 can be accomplished with no need to use any extra dedicated lubricant passage. Even in such case, the rolling performances of the rolling bearings 3 can be maintained at a favorable level.

Although the present invention has been fully described in connection with the embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

A, B . . . Flexible wire assembly
1 . . . Outer tube
2 . . . Inner wire
2a . . . Input end
2b . . . Output end
3 . . . Rolling bearing
4I . . . Inner ring spring element
4O . . . Outer ring spring element
5 . . . Joint member
6 . . . Male screw member
7 . . . Throughhole
8 . . . Externally threaded portion
10 . . . Flange portion (Connecting member)
13 . . . Female screw member
16 . . . Internally threaded portion
18 . . . Rotary shaft
19 . . . Coupling element
20 . . . Wire side member
20a . . . Radially extending groove
21 . . . Shaft side member
21a . . . Projection
22 . . . Speed reducing mechanism
22a . . . Input shaft
22b . . . Output shaft
30 . . . Rotary mechanism
35 . . . Rotary encoder (Position detecting unit)
37 . . . Rotary drive source
40 . . . Linear motion mechanism
47 . . . Linear encoder (Position detecting unit)

What is claimed is:

1. A flexible wire assembly which comprises:

a flexible outer tube;

a flexible inner wire rotatably extending in the flexible outer tube and having an input end of rotation and an output end of rotation opposite to each other;

a plurality of rolling bearings for rotatably supporting the flexible inner wire;

spring elements interposed between the neighboring rolling bearings for applying respective preloads to the rolling bearings; and a speed reducing mechanism drivingly connected with the rotation output end of the inner wire for reducing the speed of the rotation of the inner wire and outputting the rotation of the inner wire, wherein each of the rolling bearings has an inner ring and an outer ring and in which the spring elements includes an inner ring spring element in the form of a coiled compression spring for applying the preload to the inner ring and an outer ring spring element in the form of a coiled compression spring for applying the preload to the outer ring, the inner and outer ring spring elements being arranged alternately in a direction lengthwise of the inner wire.

2. The flexible wire assembly as claimed in claim 1, further comprising a rotary drive source drivingly connected with the input end of the inner wire for rotatably driving the inner wire.

3. The flexible wire assembly as claimed in claim 1, further comprising a rotary mechanism provided on an output side of the speed reducing mechanism for driving a terminal output unit with a rotary output, the speed of which has been reduced by the speed reducing mechanism.

4. The flexible wire assembly as claimed in claim 3, further comprising a position detecting unit for detecting an operational position of the rotary mechanism.

5. The flexible wire assembly as claimed in claim 1, further comprising a linear motion mechanism provided on an output side of the speed reducing mechanism for translating a rotary output, the speed of which has been reduced by the speed reducing mechanism, into a linear motion mechanism and then causing a terminal output unit to undergo the linear motion.

6. The flexible wire assembly as claimed in claim 5, further comprising a position detecting unit for detecting an operational position of the linear motion mechanism.

7. The flexible wire assembly as claimed in claim 1, further comprising a joint member provided at opposite ends of or one of the opposite ends of the outer tube for detachably connecting the outer tube with another component part.

8. The flexible wire assembly as claimed in claim 7, wherein the joint member comprises a tubular male screw member having an inner periphery formed with a throughhole for passage of the inner wire therethrough and also having an outer periphery formed with an externally threaded portion, the tubular male screw member having a first axial end received within the outer tube, and a tubular female screw member having an inner periphery formed with an internally threaded portion threadingly engageable with the externally threaded portion and also having a first end mounted on an outer diametric portion of the outer tube, and further comprising a connecting member provided in one of the male screw member and the female screw member for connection with the component part.

9. The flexible wire assembly as claimed in claim 1, further comprising a coupling element provided at opposite ends of or one of the opposite ends of the inner wire for connecting it with a rotary shaft that is rotatably supported in face to face relation with the opposite ends or one of the opposite ends of the inner wire.

10. The flexible wire assembly as claimed in claim 9, in which the coupling element comprises a wire side member rotatable together with the inner wire and a shaft side member rotatable together with the rotary shaft, the wire side member and the shaft side member having respective mating end faces that confront each other, one of the mating end faces having a radially extending groove defined therein while the other of the mating end faces has an axially extending projection defined therein and engageable in the radially extending groove, the inner wire and the rotary shaft being drivingly connected with each other by connecting the wire side member with the shaft side member with the axially extending projection engaged in the radially extending groove.

11. The flexible wire assembly as claimed in claim 1, wherein a lubricant is filled in or is allowed to flow through the rolling bearings within the outer tube.

* * * * *